US012658286B2

(12) United States Patent
Hosoumi et al.

(10) Patent No.: US 12,658,286 B2
(45) Date of Patent: Jun. 16, 2026

(54) PROPERTY PREDICTION SYSTEM

(71) Applicant: Semiconductor Energy Laboratory Co., Ltd., Kanagawa-ken (JP)

(72) Inventors: Shunsuke Hosoumi, Fujisawa (JP); Shuntaro Kochi, Yokohama (JP); Kunihiko Suzuki, Isahara (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 1140 days.

(21) Appl. No.: 17/637,671

(22) PCT Filed: Aug. 17, 2020

(86) PCT No.: PCT/IB2020/057715
§ 371 (c)(1),
(2) Date: Feb. 23, 2022

(87) PCT Pub. No.: WO2021/038362
PCT Pub. Date: Mar. 4, 2021

(65) Prior Publication Data
US 2022/0277815 A1 Sep. 1, 2022

(30) Foreign Application Priority Data

Aug. 29, 2019 (JP) .................................. 2019-156559

(51) Int. Cl.
*G16C 20/70* (2019.01)
*G06N 5/04* (2023.01)
(Continued)

(52) U.S. Cl.
CPC .............. *G16C 20/70* (2019.02); *G06N 5/04* (2013.01); *H05B 33/145* (2013.01); *H10K 50/11* (2023.02)

(58) Field of Classification Search
CPC .................................................... G16C 20/70
See application file for complete search history.

(56) References Cited

U.S. PATENT DOCUMENTS

| 7,523,028 | B2 | 4/2009 | Nakamura |
| 7,676,354 | B2 | 3/2010 | Nakamura |
| | | (Continued) | |

FOREIGN PATENT DOCUMENTS

| CN | 107025318 A | 8/2017 |
| CN | 111051876 A | 4/2020 |
| | (Continued) | |

OTHER PUBLICATIONS

International Search Report (Application No. PCT/IB2020/057715) Dated Nov. 24, 2020.

(Continued)

*Primary Examiner* — William D Young
(74) *Attorney, Agent, or Firm* — Husch Blackwell LLP

(57) ABSTRACT

A property prediction system is provided. An input portion, a processing portion, an arithmetic portion, and an output portion are included; the input portion has a function of supplying the structure of a light-emitting device or the properties of the light-emitting device; the processing portion has a function of generating a learning data set or data that is used for property prediction and a function of quantifying the molecular structure of an organic compound; the arithmetic portion has a function of performing supervised learning on the basis of the learning data set and a function of making an inference of the properties of the light-emitting device from the data on the basis of the learning result of the supervised learning; and the output portion has a function of providing the result of the inference. Thus, the properties of the light-emitting device including a layer containing an organic compound are predicted.

9 Claims, 11 Drawing Sheets

(51) Int. Cl.
H05B 33/14 (2006.01)
H10K 50/11 (2023.01)

(56) References Cited

U.S. PATENT DOCUMENTS

| | | | |
|---|---|---|---|
| 7,828,628 | B2 | 11/2010 | Aoki et al. |
| 10,776,712 | B2 | 9/2020 | Oono et al. |
| 11,017,314 | B2 | 5/2021 | Yoo et al. |
| 2008/0133188 | A1 | 6/2008 | Nakamura |
| 2009/0055151 | A1 | 2/2009 | Nakamura |
| 2011/0005143 | A1 | 1/2011 | Aoki et al. |
| 2017/0124482 | A1 | 5/2017 | Yoo et al. |
| 2017/0161635 | A1 | 6/2017 | Oono et al. |
| 2020/0349451 | A1 | 11/2020 | Suzuki et al. |
| 2020/0387831 | A1 | 12/2020 | Oono et al. |
| 2021/0241176 | A1 | 8/2021 | Yoo et al. |
| 2022/0414499 | A1 | 12/2022 | Hosoumi et al. |

FOREIGN PATENT DOCUMENTS

| | | | |
|---|---|---|---|
| EP | 3 168 765 | A1 | 5/2017 |
| JP | 2008-138097 | A | 6/2008 |
| JP | 2008-139097 | A | 6/2008 |
| JP | 2012-004181 | A | 1/2012 |
| JP | 2017-091526 | A | 5/2017 |
| JP | 2019-502988 | | 1/2019 |
| KR | 10-1635911 | | 7/2016 |
| KR | 2017-0052344 | A | 5/2017 |
| WO | WO 2017/094899 | A1 | 6/2017 |
| WO | WO 2019/048965 | A1 | 3/2019 |

OTHER PUBLICATIONS

Written Opinion (Application No. PCT/IB2020/057715) Dated Nov. 24, 2020.

<u>100</u>

<u>100</u>

$$a=x_1w_1+x_2w_2+b$$

FIG. 6A
50
51_m
51_2
51_1
52_1
·Information on light-emitting device 10_1
53_1
·Properties of light-emitting device 10_1
FIG. 6B
50
51_m
51_2
51_1
52_1 ·Information on light-emitting device 10_1
·First property of light-emitting device 10_1
53_1
·Second property of light-emitting device 10_1
FIG. 6C
52_1
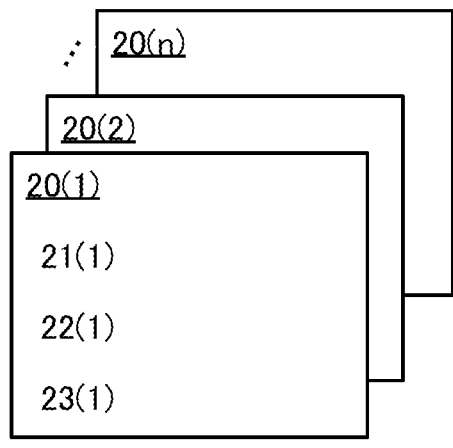
20(n)
20(2)
20(1)
21(1)
22(1)
23(1)
FIG. 6D
52_1
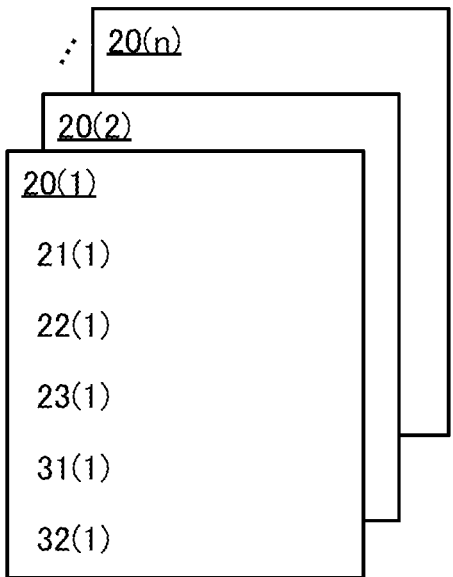
20(n)
20(2)
20(1)
21(1)
22(1)
23(1)
31(1)
32(1)

FIG. 7

FIG. 8A
Circular type
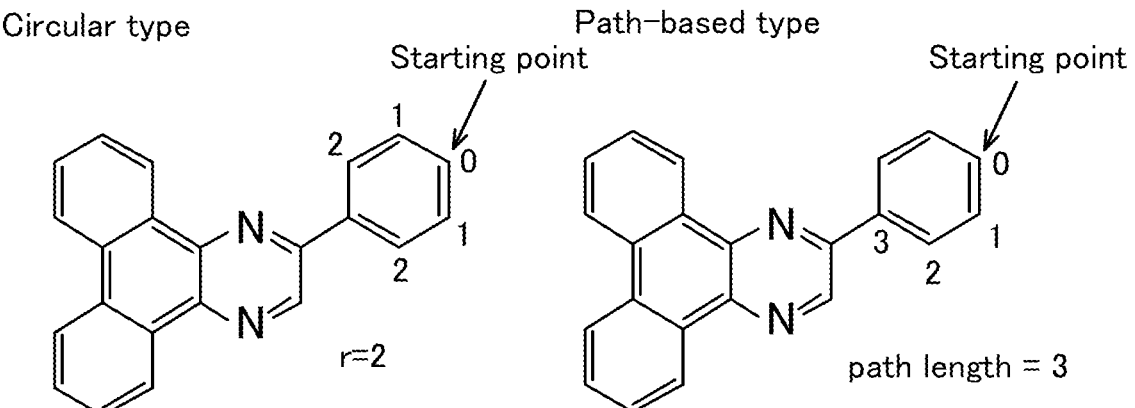
r=2
FIG. 8B
Path-based type
Starting point
path length = 3
FIG. 8C
Substructure keys type
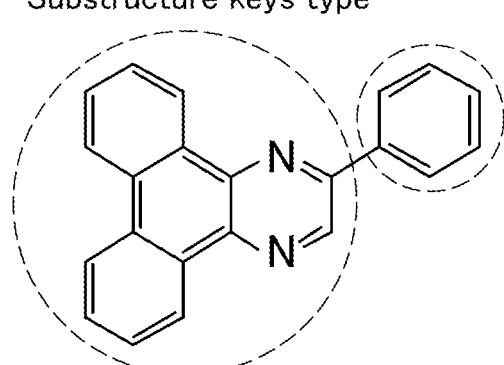
FIG. 8D
Atom pair type
Starting point
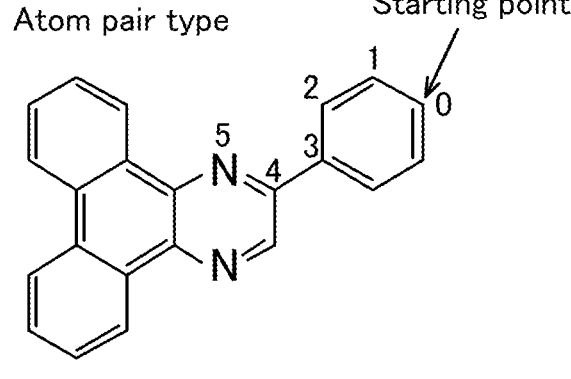

c%10ccc(n9c1ccccc1c8cc(c7cccc(c6
cccc(c5cnc4c2ccccc2c3ccccc4n5)
c6)c7)ccc89)cc%10

| No. | 1 | 2 | 3 | 4 | 5 |
|---|---|---|---|---|---|
| Molecular structure | | | | | |
| ①Circular type Morgan Fingerprint (r = 6) | | | | | |
| ②Path-based type RDK Fingerprint (L = 8) | | | | | |
| ③Substructure keys type Avalon Fingerprint | | | | | |
| ④Atom pair type Hash atom pair | | | | | |

[Combination of two types]

Circular type          Atom pair type

[Combination of three types]

Circular type      Substructure Keys type      Atom pair type

PROPERTY PREDICTION SYSTEM

This application is a 371 of international application PCT/IB2020/057715 filed on Aug. 17, 2020 which is incorporated herein by reference.

TECHNICAL FIELD

One embodiment of the present invention relates to a method of predicting the properties of a light-emitting device. One embodiment of the present invention relates to a property prediction system predicting the properties of a light-emitting device.

BACKGROUND ART

A light-emitting device including an EL (Electro Luminescence) layer between a pair of electrodes (also referred to as a light-emitting element) has characteristics such as thinness, light weight, high-speed response to input signals, and low power consumption; thus, a display including such a light-emitting device has attracted attention as a next-generation flat panel display.

A light-emitting device using an organic compound for an EL layer (also referred to as an organic EL device or an organic EL element) shows various characteristics when various organic compounds are stacked. However, there are more than a million kinds of organic compounds even as only known organic compounds. Furthermore, in the case where a light-emitting device has a stacked-layer structure, the thickness of each stacked layer and the concentration ratio of an organic compound therein also affect the properties of the light-emitting device. Therefore, much energy is needed for the optimization of a light-emitting device structure (also simply referred to as an element structure).

In recent years, a method of classification, estimation, prediction, or the like employing a method such as machine learning has advanced significantly. Selection and prediction by a neural network (particularly, deep learning) have significantly improved in performance, and produced excellent effects in various fields. Patent Document 1 discloses a novel substance searching method using machine learning and a device thereof.

REFERENCE

Patent Document

[Patent Document 1] Japanese Published Patent Application No. 2017-91526

SUMMARY OF THE INVENTION

Problems to be Solved by the Invention

The optimization of an organic EL device structure largely depends on an expert. A technique of an organic EL device covers a plurality of academic regions, and knowledge of organic chemistry, semiconductor physics, electrical engineering, and the like is required; thus, high skill is needed. In addition, many long years are needed for optimization, so that the process of the optimization has to be stored.

In view of the above, an object of one embodiment of the present invention is to provide a method of predicting the properties of a light-emitting device. Another object of one embodiment of the present invention is to provide a system predicting the properties of a light-emitting device. Another object of one embodiment of the present invention is to provide a generation method of a learning data set.

Note that the description of these objects does not preclude the existence of other objects. One embodiment of the present invention does not have to achieve all these objects. Other objects will be apparent from the descriptions of the specification, the drawings, the claims, and the like, and other objects can be derived from the descriptions of the specification, the drawings, the claims, and the like.

Means for Solving the Problems

In view of the above problems, one embodiment of the present invention provides a system in which information on a plurality of light-emitting devices and the properties of the plurality of light-emitting devices are used for machine learning, so that, from information on a light-emitting device, the properties of the light-emitting device are predicted.

One embodiment of the present invention is a property prediction system that predicts properties of a light-emitting device including a layer containing an organic compound. The property prediction system includes an input portion, a processing portion, an arithmetic portion, and an output portion. The input portion has a function of supplying the structure of the light-emitting device or the properties of the light-emitting device. The processing portion has a function of generating a learning data set or data that is used for property prediction and a function of quantifying the molecular structure of an organic compound. The arithmetic portion has a function of performing supervised learning on the basis of the learning data set and a function of making an inference of the properties of the light-emitting device from the data on the basis of the learning result of the supervised learning. The output portion has a function of providing the result of the inference.

In the above property prediction system, it is preferable that the light-emitting device include a plurality of layers, that one or more of the plurality of layers contain one or more organic compounds, that the learning data set include a plurality of pieces of learning data, that each of the plurality of pieces of learning data include input data and teacher data with respect to the input data, that the input data include the stacking order of the plurality of layers, that the molecular structure of the one or more organic compounds contained in one or more of the plurality of layers, each thickness of the plurality of layers, and the concentration ratios of a plurality of organic compounds in a layer containing the plurality of organic compounds, and that the teacher data include the properties of the light-emitting device with respect to the input data.

In the above property prediction system, the properties of the light-emitting device are preferably any one or more of a luminance—current density property, a current efficiency—luminance property, a luminance—voltage property, a current—voltage property, an external quantum efficiency—luminance property, a chromaticity—luminance property, an emission spectrum, and reliability.

Another embodiment of the present invention is a property prediction system that predicts the properties of a light-emitting device including a layer containing an organic compound. The property prediction system includes an input portion, a processing portion, an arithmetic portion, and an output portion. A learning data set and data that is used for property prediction are input to the input portion. The processing portion has a function of quantifying the molecular structure of an organic compound. The arithmetic portion has a function of performing supervised learning on the basis of the learning data set and a function of making an inference of the reliability of the light-emitting device from the data on the basis of the learning result of the supervised learning. The output portion has a function of providing the result of the inference. The leaning data set includes a plurality of pieces of learning data, and each of the plurality of pieces of learning data includes a plurality of pieces of input data and a plurality of pieces of teacher data with respect to the input data. The input data includes the stacking order of the plurality of layers, the molecular structure of one or more organic compounds contained in each of the plurality of layers, each thickness of the plurality of layers, the concentration ratios of a plurality of organic compounds in a layer containing the plurality of organic compounds, and an external quantum efficiency—luminance property of the light-emitting device. The teacher data includes the reliability of the light-emitting device with respect to the input data.

In the above property prediction system, the quantification of the molecular structure of the organic compound is preferably performed by quantitative structure-activity relationship or a fingerprinting method.

In the above property prediction system, it is preferable that a neural network be used for the supervised learning and the neural network include two or more hidden layers between an input layer and an output layer.

In the above property prediction system, it is preferable that a memory portion be included and a learned model generated by the supervised learning be stored in the memory portion.

Effect of the Invention

According to one embodiment of the present invention, a method of predicting the properties of a light-emitting device can be provided. According to another embodiment of the present invention, a system predicting the properties of a light-emitting device can be provided. According to another embodiment of the present invention, a generation method of a learning data set can be provided.

Note that the effects of embodiments of the present invention are not limited to the effects listed above. The effects listed above do not preclude the existence of other effects. Note that the other effects are effects that are not described in this section and will be described below. The effects that are not described in this section can be derived from the descriptions of the specification, the drawings, and the like and can be extracted from these descriptions by those skilled in the art. Note that one embodiment of the present invention is to have at least one of the effects listed above and/or the other effects. Accordingly, depending on the case, one embodiment of the present invention does not have the effects listed above in some cases.

BRIEF DESCRIPTION OF THE DRAWINGS

FIG. 6A to FIG. 6D are diagrams illustrating a learning data set.

FIG. 7 is a diagram illustrating a converting method of a molecular structure by a fingerprinting method.

FIG. 8A to FIG. 8D are diagrams illustrating kinds of fingerprinting methods.

FIG. 10 is a diagram showing kinds of fingerprinting methods and duplicating notations.

MODE FOR CARRYING OUT THE INVENTION

Figure 1A:
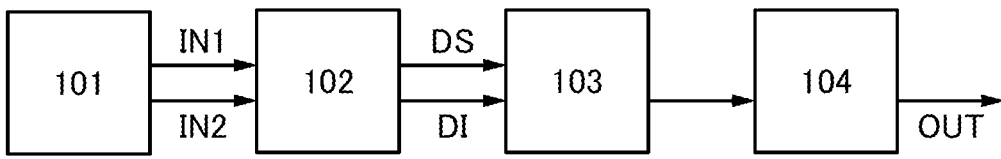
FIG. 1A and FIG. 1B are diagrams illustrating a property prediction system.

Embodiments are described in detail with reference to the drawings. Note that the present invention is not limited to the following description, and it will be readily understood by those skilled in the art that modes and details of the present invention can be modified in various ways without departing from the spirit and scope of the present invention. Therefore, the present invention should not be interpreted as being limited to the description of the embodiment below.

Note that in the structures of the invention described below, the same portions or portions having similar functions are denoted by the same reference numerals in different drawings, and description thereof is not repeated. Furthermore, the same hatch pattern is used for the portions having similar functions, and the portions are not especially denoted by reference numerals in some cases.

In addition, the position, size, range, or the like of each structure shown in drawings does not represent the actual position, size, range, or the like in some cases for easy understanding. Therefore, the disclosed invention is not necessarily limited to the position, size, range, or the like disclosed in the drawings.

Furthermore, ordinal numbers such as "first," "second," and "third" used in this specification are used in order to avoid confusion among components, and the terms do not limit the components numerically.

Embodiment 1

In this embodiment, a property prediction system predicting the properties of a light-emitting device and a method of predicting the properties of a light-emitting device will be described.

<Structure Example of Property Prediction System>

Structure examples of a property prediction system will be described with reference to FIG. 1A and FIG. 1B.

FIG. 1A is a diagram illustrating a structure example of a property prediction system 100. The property prediction system 100 includes an input portion 101, a processing portion 102, an arithmetic portion 103, and an output portion 104.

The input portion 101 and the processing portion 102 are connected to each other through a transmission path. The processing portion 102 and the arithmetic portion 103 are connected to each other through a transmission path. The arithmetic portion 103 and the output portion 104 are connected to each other through a transmission path. Note that each of the input portion 101, the processing portion 102, the arithmetic portion 103, and the output portion 104 may be connected through a transmission path.

Note that the transmission path includes a network such as a local area network (LAN) or the Internet. In addition, for the network, wired or wireless communication or wired and wireless communication can be used.

Furthermore, in the case where a wireless communication is used for the network, besides near field communication means such as Wi-Fi (registered trademark) and Bluetooth (registered trademark), a variety of communication means such as the third generation mobile communication system (3G)-compatible communication means, LTE (sometimes also referred to as 3.9G)-compatible communication means, the fourth generation mobile communication system (4G)-compatible communication means, or the fifth generation mobile communication system (5G)-compatible communication means can be used.

The input portion 101 has a function of supplying data IN1 and data IN2 to the processing portion 102. Information on a light-emitting device and data such as the properties of the light-emitting device are included in each of the data IN1 and the data IN2. The data IN2 includes at least the information on the light-emitting device. In some cases, the data IN2 includes the data such as the properties of the light-emitting device.

The data IN1 and the data IN2 may be supplied to the processing portion 102 at the same timing or different timings. In the case where the data is supplied at different timings, it is preferable that the data IN1 be supplied to the processing portion 102, and then the data IN2 be supplied to the processing portion 102.

The processing portion 102 has a function of generating a learning data set DS from the data IN1. Furthermore, the processing portion 102 has a function of generating data DI used for property prediction from the data IN2. In addition, the processing portion 102 has a function of quantifying the molecular structure of an organic compound. Note that the processing portion 102 may have a function of quantifying the structure of an inorganic compound.

The arithmetic portion 103 has a function of performing machine learning. For example, the arithmetic portion 103 preferably has a function of performing supervised learning on the basis of the learning data set DS. The arithmetic portion 103 preferably has a function of making an inference of the properties of a light-emitting device from the data DI used for property prediction on the basis of the learning result of the supervised learning. By the supervised learning, the accuracy of the inference of the properties of a light-emitting device can be improved. Note that a learned model may be generated by the supervised learning.

For the supervised learning, a neural network (especially, deep learning) is preferably used. For the deep learning, a convolutional neural network (CNN), a recurrent neural network (RNN), an autoencoder (AE), a variational autoencoder (VAE), random forest, a support vector machine, gradient boosting, a generative adversarial network (GAN), or the like is preferably used, for example.

Note that a product-sum operation is performed in a neural network. When the product-sum operation is performed by hardware, the arithmetic portion 103 preferably includes a product-sum operation circuit. A digital circuit may be used or an analog circuit may be used as the product-sum operation circuit. Note that the product-sum operation may be performed on software using a program.

The arithmetic portion 103 may have a function of performing semi-supervised learning as machine learning. Data on the properties of a light-emitting device is supplied to learning data as teacher data (also referred to as a teacher signal, a correct label, or the like); in order to prepare the teacher data, a light-emitting device needs to be actually fabricated to measure the properties of the light-emitting device. Since the number of pieces of learning data included in a learning data set in semi-supervised learning may be smaller than in supervised learning, an inference can be made while the time spent to generate learning data is shortened.

The output portion 104 has a function of providing data OUT. The data OUT includes the result of the inference.

In the above manner, the property prediction system predicting the properties of a light-emitting device is formed.

Note that the structure of the property prediction system 100 is not limited to the above. For example, as illustrated in FIG. 1B, the memory portion 105 may be included in addition to the input portion 101, the processing portion 102, the arithmetic portion 103, and the output portion 104.

The memory portion 105 has a function of storing the learned model generated by the arithmetic portion 103. When the property prediction system 100 includes the memory portion 105, the properties of a light-emitting device can be predicted on the basis of the learned model. Thus, the learned model is generated in advance, whereby supervised learning is not necessary when the properties of a light-emitting device are predicted. Therefore, the time needed for the prediction of the properties of a light-emitting device can be shortened.

The memory portion 105 and the arithmetic portion 103 are connected to each other through a transmission path. Note that the memory portion 105 may be connected to each of the input portion 101, the processing portion 102, the arithmetic portion 103, and the output portion 104 through a transmission path.

The above is the description of the structure example of the property prediction system.

<Method of Predicting Properties>

Next, examples of a method of predicting the properties of a light-emitting device will be described with reference to FIG. 2, FIG. 3, FIG. 4A, and FIG. 4B.

Figure 2:
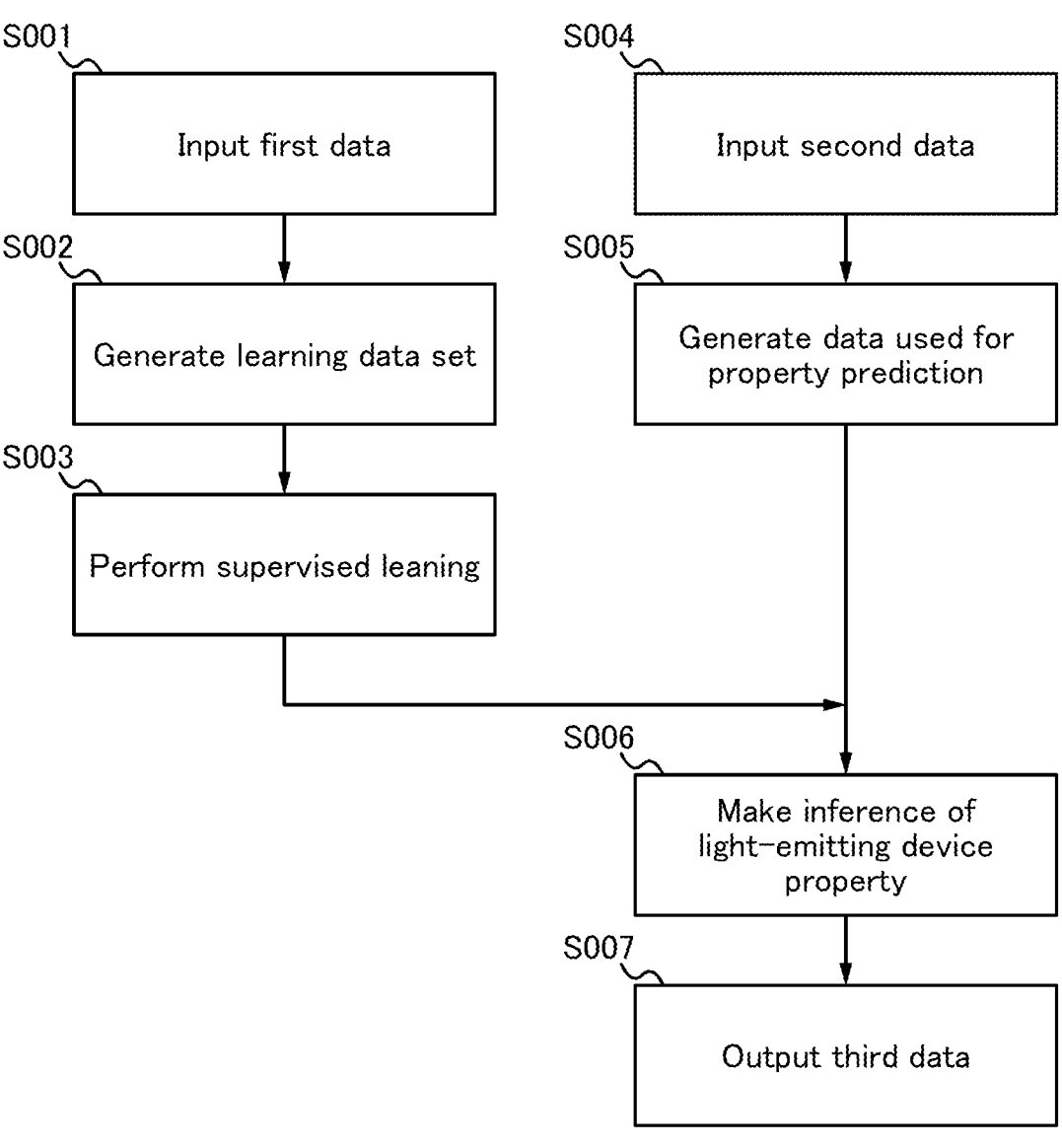
FIG. 2 is a flow chart showing a method of predicting the properties of a light-emitting device.

FIG. 2 is a flow chart showing an example of a method of predicting the properties of a light-emitting device. The method of predicting the properties of a light-emitting device includes Step S001 to Step S007. Step S001 to Step 003 are steps of supervised learning, and Step S004 to Step S007 are steps of making an inference of the properties of a light-emitting device.

Step S001 is a step of inputting first data. Step S001 is performed in the input portion 101 illustrated in FIG. 1A and FIG. 1B. The first data corresponds to the data IN1 illustrated in FIG. 1A and FIG. 1B. That is, the first data includes information on a light-emitting device and data such as the properties of the light-emitting device.

Step S002 is a step of generating a learning data set from the first data. Step S002 is performed in the processing portion 102 illustrated in FIG. 1A and FIG. 1B. The learning data set corresponds to the learning data set DS illustrated in FIG. 1A and FIG. 1B.

In the case where the first data includes the molecular structure of an organic compound, Step S002 includes a step of quantifying the molecular structure of the organic compound. Note that the quantified molecular structure of the organic compound is included in the learning data set.

Furthermore, in the case where the first data includes the molecular structure of an inorganic compound, Step S002 may include a step of quantifying the molecular structure of the inorganic compound. Note that the quantified molecular structure of the inorganic compound may be included in the learning data set.

Step S003 is a step of performing supervised learning on the basis of the learning data set. Step S003 is performed in the arithmetic portion 103 illustrated in FIG. 1A and FIG. 1B. For the supervised learning, a neural network (especially, deep learning) is preferably used. Note that by the supervised learning, a learned model for predicting the properties of a light-emitting device may be generated.

Step S004 is a step of inputting second data. Step S004 is performed in the input portion 101 illustrated in FIG. 1A and FIG. 1B. The second data corresponds to the data IN2 illustrated in FIG. 1A and FIG. 1B. That is, the second data includes the information on the light-emitting device. In some cases, the second data includes the data such as the properties of the light-emitting device.

Note that Step S004 may be performed at the same time as Step S001, during Step S001 to Step S003, or after Step S003.

Step S005 is a step of generating data used for the property prediction from the second data. Step S005 is performed in the processing portion 102 illustrated in FIG. 1A and FIG. 1B. That is, the data corresponds to the data DI used for the property prediction illustrated in FIG. 1A and FIG. 1B.

In the case where the second data includes the molecular structure of an organic compound, Step S005 includes a step of quantifying the molecular structure of the organic compound. Note that the quantified molecular structure of the organic compound is included in the data.

Furthermore, in the case where the second data includes the molecular structure of an inorganic compound, Step S005 may include a step of quantifying the molecular structure of the inorganic compound. Note that the quantified molecular structure of the inorganic compound may be included in the data.

Step S006 is a step of making an inference of the properties of the light-emitting device from the data on the basis of the learning result of the supervised learning. Step S006 is performed in the arithmetic portion 103 illustrated in FIG. 1A and FIG. 1B.

Step S007 is a step of outputting third data. Step S007 is performed in the output portion 104 illustrated in FIG. 1A and FIG. 1B. The third data corresponds to the data OUT illustrated in FIG. 1A and FIG. 1B. That is, the third data includes the result of the inference.

In the above manner, the properties of a light-emitting device can be predicted.

Figure 3:
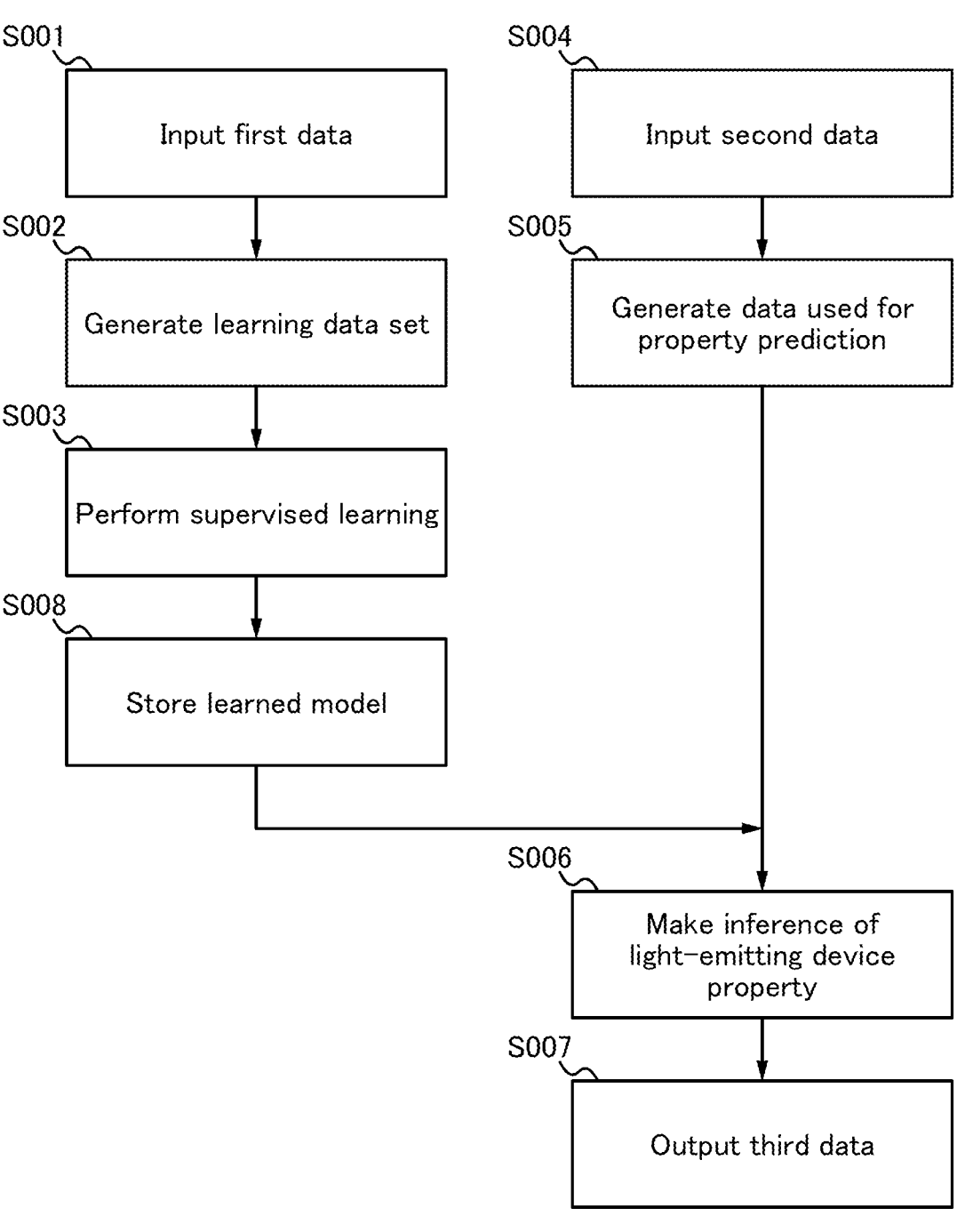
FIG. 3 is a flow chart showing a method of predicting the properties of a light-emitting device.

Note that the method of predicting the properties of a light-emitting device is not limited to the above. For example, as illustrated in FIG. 3, the method of predicting the properties of a light-emitting device may include Step S008 after Step S003.

Step S008 is a step of storing a learned model generated in Step S003. Note that the learned model is stored in the memory portion 105 illustrated in FIG. 1B. When the learned model is generated in advance, the steps of Step S001 to Step S003 can be omitted in the prediction of the properties of a light-emitting device. Thus, the time needed for the prediction of the properties of a light-emitting device can be shortened.

<<Neural Network>>

Here, a neural network that can be used for supervised learning will be described.

Figures 4A, 4B:
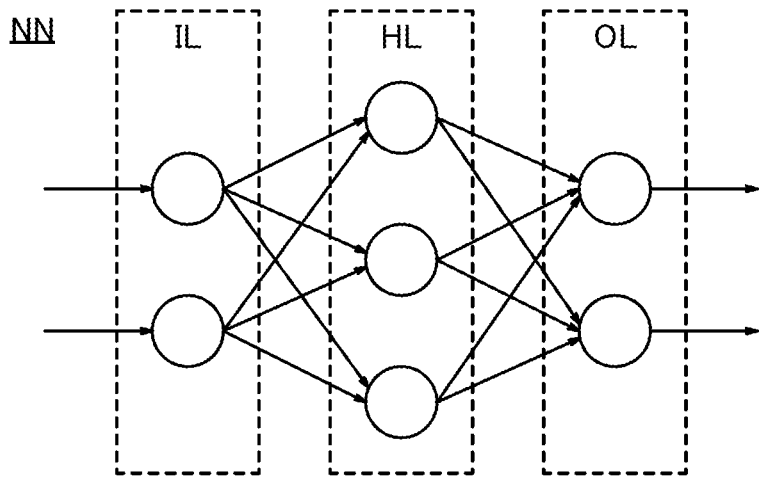
FIG. 4A and FIG. 4B are diagrams illustrating a neural network structure.

As illustrated in FIG. 4A, a neural network NN can be formed of an input layer IL, an output layer OL, and a hidden layer HL. The input layer IL, the output layer OL, and the hidden layer HL each include one or more neurons (units). Note that the hidden layer HL may be composed of one layer or two or more layers. A neural network including two or more hidden layers HL can also be referred to as a deep neural network (DNN). Learning using a deep neural network can also be referred to as deep learning.

Input data is input to each neuron in the input layer IL. A signal output from a neuron in the previous layer or the subsequent layer is input to each neuron in the hidden layer HL. To each neuron in the output layer OL, output signals of the neurons in the previous layer are input. Note that each neuron may be connected to all the neurons in the previous and subsequent layers (full connection), or may be connected to some of the neurons.

FIG. 4B illustrates an example of an arithmetic operation with the neurons. Here, a neuron N and two neurons in the previous layer which output signals to the neuron N are illustrated. An output $x_1$ of a neuron in the previous layer and an output $x_2$ of a neuron in the previous layer are input to the neuron N. Then, in the neuron N, a total sum $x_1w_1+x_2w_2$ of a multiplication result $(x_1w_1)$ of the output $x_1$ and a weight $w_1$ and a multiplication result $(x_2w_2)$ of the output $x_2$ and a weight $w_2$ is calculated, and then a bias b is added as necessary, so that the value $a=x_1w_1+x_2w_2+b$ is obtained. Then, the value a is converted with an activation function h, and an output signal $y=ah$ is output from the neuron N. As the activation function h, for example, a sigmoid function, a tan h function, a softmax function, a ReLU function, a threshold function, or the like can be used.

In this manner, the arithmetic operation with the neurons includes the arithmetic operation that sums the products of the outputs and the weights of the neurons in the previous layer, that is, the product-sum operation $(x_1w_1+x_2w_2$ described above). This product-sum operation may be performed using a program on software or may be performed using hardware. In the case where the product-sum operation is performed by hardware, a product-sum operation circuit can be used. A digital circuit may be used or an analog circuit may be used as this product-sum operation circuit. In the case where an analog circuit is used as the product-sum operation circuit, the circuit scale of the product-sum operation circuit can be reduced, or higher processing speed and lower power consumption can be achieved by reduced frequency of access to a memory.

The product-sum operation circuit may be composed of transistors including silicon (such as single crystal silicon) in a channel formation region (hereinafter also referred to as Si transistors), or may be composed of transistors including an oxide semiconductor in a channel formation region (hereinafter also referred to as OS transistors). An OS transistor is particularly suitable for a transistor included in an analog memory of the product-sum operation circuit because of its extremely low off-state current. Note that the product-sum operation circuit may be formed using both a Si transistor and an OS transistor.

In the case where the product-sum operation is performed by hardware, a product-sum operation circuit is preferably included in the arithmetic portion 103 that is included in the property prediction system 100.

The above is the description of the neural network. Note that in one embodiment of the present invention, deep learning is preferably used. That is, a neural network including two or more hidden layers HL is preferably used.

The above is the description of the examples of a method of predicting the properties of a light-emitting device.

<Detail of Method of Predicting Properties of Light-Emitting Device>

A method of predicting the properties of a light-emitting device will be described in detail below with reference to FIG. 5 to FIG. 11B.

<<Structure of Light-Emitting Device>>

First, the structure of a light-emitting device will be described.

A light-emitting device is basically a device in which a layer containing a light-emitting material (also referred to as a light-emitting layer) is sandwiched between a pair of electrodes. By application of voltage to the device, light emitted from the light-emitting material can be obtained. An organic compound or an inorganic compound can be used as the light-emitting material. Note that the light-emitting layer may be provided using one organic compound or one inorganic compound. Alternatively, the light-emitting layer may be provided in which a plurality of organic compounds are mixed or stacked. Alternatively, the light-emitting layer may be provided in which a plurality of inorganic compounds are mixed or stacked. Alternatively, the light-emitting layer may be provided in which an organic compound and an inorganic compound are mixed or stacked. In the following, a light-emitting device using an organic compound as a light-emitting material is described as an example.

Figure 5:
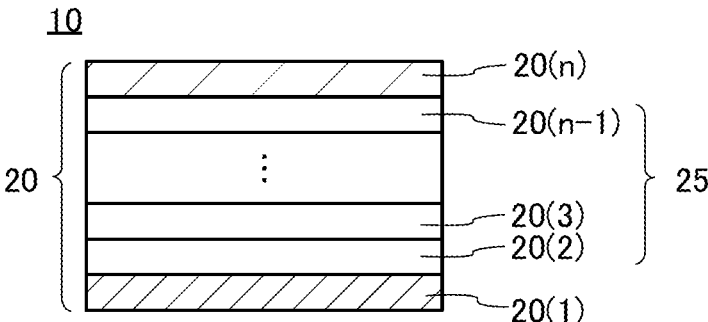
FIG. 5 is a diagram illustrating a light-emitting device structure.

FIG. 5 is a schematic diagram illustrating the structure of a light-emitting device 10. The light-emitting device 10 has a structure in which a plurality of layers are stacked. For example, the light-emitting device 10 includes a layer 20 in which n layers (n is an integer greater than or equal to 3) are stacked. In other words, the layer 20 includes a layer 20(1) to a layer 20($n$). Note that a substrate is not illustrated in FIG. 5.

The light-emitting device has a structure in which a layer containing a light-emitting material is sandwiched between a pair of electrodes. Thus, the layer 20(1) functions as one of an anode and a cathode of the light-emitting device 10, and the layer 20($n$) functions as the other of the anode and the cathode of the light-emitting device. Note that the anode and/or the cathode of the light-emitting device 10 are not limited to a single layer and may be stacked layers. At this time, the one of the anode and the cathode of the light-emitting device 10 includes the layer 20(1) to the layer 20($j$) ($j$ is an integer greater than or equal to 1 and less than or equal to ($n$−2)), and the other of the anode and the cathode of the light-emitting device 10 includes the layer 20($k$) to the layer 20($n$) ($k$ is an integer greater than or equal to ($j$+2) or less than or equal to n). Hereinafter, each of the anode and the cathode of the light-emitting device 10 is regarded as having a single-layer structure for simple description.

In the case where each of the anode and the cathode of the light-emitting device 10 is a single layer, some or all of the layer 20(2) to the layer 20($n$−1) contain an organic compound. Furthermore, any one or more of the layer 20(2) to the layer 20($n$−1) contain a light-emitting material. The layer 20(2) to the layer 20($n$−1) are all regarded as layers containing an organic compound below. The layers (the layer 20(2) to the layer 20($n$−1)) positioned between the pair of electrodes are collectively referred to as an intermediate layer 25 in some cases.

In the case where n is 3, the intermediate layer 25 has a single-layer structure. That is, the intermediate layer 25 is formed of only the layer 20(2). The structure of the light-emitting device 10 in which n is 3 is referred to as a single structure in some cases. In the case where n is 4 or more, the intermediate layer 25 is formed of a plurality of layers. That is, the intermediate layer 25 has a stacked-layer structure.

[Light-Emitting Device Whose Intermediate Layer has Stacked-Layer Structure]

The light-emitting device 10 whose intermediate layer has a stacked-layer structure will be described below.

In the case where n is 5, the intermediate layer 25 has a stacked-layer structure of three layers. At this time, the intermediate layer 25 can have a stacked-layer structure of a hole-transport layer, a light-emitting layer, and an electron-transport layer. This can increase the current efficiency and external quantum efficiency of the light-emitting device 10. In the case where n is 6 or more, the intermediate layer 25 has a structure in which four or more layers are stacked. Thus, any one or more of the hole-transport layer, the light-emitting layer, and the electron-transport layer can have a stacked-layer structure.

In the case where the layer 20(1) functions as an anode and the layer 20($n$) functions as a cathode, the intermediate layer 25 has a structure in which the hole-transport layer, the light-emitting layer, and the electron-transport layer are stacked in this order. Note that in the case where the layer 20(1) functions as a cathode and the layer 20($n$) functions as an anode, the stacking order is reversed.

Note that when the thicknesses of the anode, the hole-transport layer, the light-emitting layer, the electron-transport layer, and the cathode are adjusted appropriately, the properties of the light-emitting device, such as the emission efficiency and external quantum efficiency, can be improved. In other words, the properties of the light-emitting device are affected by the thickness of each of the layer 20(1) to the layer 20($n$).

In the case where n is 7, the intermediate layer 25 has a stacked-layer structure of five layers. At this time, the intermediate layer 25 can have a stacked-layer structure of a hole-injection layer, a hole-transport layer, a light-emitting layer, an electron-transport layer, and an electron-injection layer. This can further increase the current efficiency and external quantum efficiency of the light-emitting device 10. In the case where n is 8 or more, the intermediate layer 25 has a structure in which six or more layers are stacked. Thus, any one or more of the hole-injection layer, the hole-transport layer, the light-emitting layer, the electron-transport layer, and the electron-injection layer can have a stacked-layer structure.

In the case where the layer 20(1) functions as an anode and the layer 20($n$) functions as a cathode, the intermediate layer 25 has a structure in which the hole-injection layer, the hole-transport layer, the light-emitting layer, an electron-transport layer, and the electron-injection layer are stacked in this order. Note that in the case where the layer 20(1) functions as a cathode and the layer 20($n$) functions as an anode, the stacking order is reversed.

The light-emitting layer contains a light-emitting material and a plurality of materials in appropriate combination, so that fluorescence or phosphorescence of a desired emission color can be obtained. The light-emitting layer may have a stacked-layer structure having different emission colors. In that case, light-emitting substances and other substances can be different between the stacked light-emitting layers.

For example, when the light-emitting device 10 has a micro optical resonator (microcavity) structure with the layer 20(1) and the layer 20($n$) respectively serving as a reflective electrode and a semi-transmissive and semi-reflective electrode, light obtained from the light-emitting layer included in the intermediate layer 25 can be resonated between the electrodes and thus the light emitted through the layer $20(n)$ can be intensified.

Note that when the layer $20(1)$ of the light-emitting device 10 is a reflective electrode having a stacked-layer structure of a reflective conductive material and a light-transmitting conductive material (transparent conductive film), optical adjustment can be performed by adjusting the thickness of the transparent conductive film. Specifically, when the wavelength of light obtained from the light-emitting layer is $\lambda$, the electrode distance between the layer $20(1)$ and the layer $20(n)$ is preferably adjusted to around $m_1\lambda/2$ (note that $m_1$ is a natural number).

To amplify desired light (wavelength: $\lambda$) obtained from the light-emitting layer, the optical path length from the layer $20(1)$ to a region of the light-emitting layer where desired light is obtained (light-emitting region) and the optical path length from the layer $20(n)$ to the region of the light-emitting layer where desired light is obtained (light-emitting region) are preferably adjusted to around $(2m_2+1)\lambda/4$ (note that $m_2$ is a natural number). Here, the light-emitting region refers to a region where holes and electrons are recombined in the light-emitting layer.

By such optical adjustment, the spectrum of specific monochromatic light obtained from the light-emitting layer can be narrowed and light emission with high color purity can be obtained.

In the above case, the electrode distance between the layer $20(1)$ and the layer $20(n)$ can be strictly regarded as the total thickness from a reflective region in the layer $20(1)$ to a reflective region in the layer $20(n)$. However, it is difficult to precisely determine the reflective region in the layer $20(1)$ and the layer $20(n)$; hence, it is assumed that the above effect is sufficiently obtained with given positions in the layer $20(1)$ and the layer $20(n)$ being supposed to be reflective regions. Furthermore, the optical path length between the layer $20(1)$ or the layer $20(n)$ and the light-emitting layer where desired light is obtained is, to be exact, the optical path length between the reflective region in the layer $20(1)$ or the layer $20(n)$ and the light-emitting region where desired light is obtained in the light-emitting layer. However, it is difficult to precisely determine the reflective region in the layer $20(1)$ or the layer $20(n)$ and the light-emitting region in the light-emitting layer where the desired light is obtained; thus, it is assumed that the above effect can be sufficiently obtained with a given position in the layer $20(1)$ or the layer $20(n)$ being supposed to be the reflective region and a given position in the light-emitting layer where the desired light is obtained being supposed to be the light-emitting region.

In the above case, since the light-emitting device 10 has the microcavity structure, light with different wavelengths (monochromatic light) can be extracted even if the same intermediate layer 25 is used. Therefore, in the case where the light-emitting device 10 is used as a display element of a display device, separate coloring for obtaining different emission colors (e.g., RGB) is unnecessary. Therefore, high resolution can be easily achieved. In addition, a combination with coloring layers is also possible. Furthermore, the emission intensity of light with a specific wavelength in the front direction can be increased, whereby power consumption can be reduced.

Note that the light-emitting device 10 does not necessarily have a microcavity structure. In that case, light of predetermined colors (e.g., RGB) can be extracted when the light-emitting layer has a structure for emitting white light and coloring layers are provided. When the intermediate layer 25 are formed by separate coloring for obtaining different emission colors, light of predetermined colors can be extracted without providing coloring layers.

At least one of the layer $20(1)$ and the layer $20(n)$ can be a light-transmitting electrode (e.g., a transparent electrode or a semi-transmissive and semi-reflective electrode). In the case where the light-transmitting electrode is a transparent electrode, the transparent electrode has a visible light transmittance higher than or equal to 40%. In the case where the light-transmitting electrode is a semi-transmissive and semi-reflective electrode, the visible light reflectance of the semi-transmissive and semi-reflective electrode is higher than or equal to 20% and lower than or equal to 80%, preferably higher than or equal to 40% and lower than or equal to 70%. These electrodes preferably have a resistivity lower than or equal to $1\times10^{-2}$ $\Omega$cm.

In the case where the layer $20(1)$ or the layer $20(n)$ is an electrode having reflectivity (reflective electrode), the visible light reflectance of the electrode having reflectivity is higher than or equal to 40% and lower than or equal to 100%, preferably higher than or equal to 70% and lower than or equal to 100%. This electrode preferably has a resistivity lower than or equal to $1\times10^{-2}$ $\Omega$cm.

In the case where n is 5, the intermediate layer 25 has a stacked-layer structure of three layers. In that case, the intermediate layer 25 can have a stacked-layer structure of a first light-emitting layer, a charge-generation layer, and a second light-emitting layer. In other words, the light-emitting device 10 can have a tandem structure. When the light-emitting device 10 has the tandem structure, the current efficiency and external quantum efficiency of the light-emitting device 10 can be increased.

In the case where n is 6 or more, the intermediate layer 25 has a structure in which four or more layers are stacked. In that case, any one or more of a layer (sometimes referred to as a first intermediate layer) sandwiched between the layer $20(1)$ and the charge-generation layer, the charge-generation layer, and a layer (sometimes referred to as a second intermediate layer) sandwiched between the charge-generation layer and the layer $20(n)$ can have a stacked-layer structure. For example, in the case where n is 13, the first intermediate layer and the second intermediate layer can each have a structure similar to that of the intermediate layer 25 having a stacked-layer structure of the five layers.

The charge-generation layer has a function of injecting electrons into one of the first intermediate layer and the second intermediate layer and injecting holes into the other of the first intermediate layer and the second intermediate layer when voltage is applied between the layer $20(1)$ and the layer $20(n)$. Thus, when voltage is applied such that the potential of the layer $20(1)$ is higher than the potential of the layer $20(n)$, electrons are injected from the charge-generation layer into the first intermediate layer and holes are injected from the charge-generation layer into the second intermediate layer.

Note that the charge-generation layer preferably transmits visible light in terms of light extraction efficiency. Specifically, the visible light transmittance of the charge-generation layer is preferably greater than or equal to 40%. The conductivity of the charge-generation layer may be lower than the conductivity of the layer $20(1)$ or the conductivity of the layer $20(n)$.

In the case where n is 7, the intermediate layer 25 has a stacked-layer structure of five layers. In that case, the intermediate layer 25 can have a stacked-layer structure of the first light-emitting layer, a first charge-generation layer, the second light-emitting layer, a second charge-generation layer, and a third light-emitting layer. In other words, the light-emitting device 10 can have a tandem structure. When the light-emitting device 10 has the tandem structure, the current efficiency and external quantum efficiency of the light-emitting device 10 can be further increased.

In the case where n is 8 or more, the intermediate layer 25 has a structure in which six or more layers are stacked. Any one or more of a layer (sometimes referred to as a first intermediate layer) sandwiched between the layer 20(1) and the first charge-generation layer, the first charge-generation layer, a layer (sometimes referred to as a second intermediate layer) sandwiched between the first charge-generation layer and the second charge-generation layer, the second charge-generation layer, and a layer (sometimes referred to as a third intermediate layer) sandwiched between the second charge-generation layer and the layer 20(n) can have a stacked-layer structure. For example, in the case where n is 19, the first intermediate layer, the second intermediate layer, and the third intermediate layer can each have a structure similar to that of the intermediate layer 25 having a stacked-layer structure of the above five layers.

Although a structure in which the intermediate layer 25 includes one charge-generation layer and two intermediate layers or a structure in which the intermediate layer 25 includes two charge-generation layers and three intermediate layers is described, the structure is not limited thereto. The intermediate layer 25 may have a structure including three or more charge-generation layers and four or more intermediate layers. When the number of the charge-generation layers and the number of the intermediate layers are increased, the current efficiency and external quantum efficiency of the light-emitting device 10 can be increased. Note that n is preferably adjusted as appropriate in accordance with the number of layers of the charge-generation layer.

The above is the description of the light-emitting device 10 whose intermediate layer has a stacked-layer structure.

In some cases, the layer included in the intermediate layer 25 is formed by co-evaporation of a plurality of organic compounds. The layer formed by co-evaporation contains a plurality of organic compounds. Thus, the intermediate layer 25 includes a layer containing a plurality of organic compounds in some cases. When the intermediate layer 25 includes a layer containing a plurality of organic compounds, the concentration ratio of the plurality of organic compounds affects the properties of the light-emitting device.

The above is the description of the structure of a light-emitting device.

<<Properties of Light-Emitting Device>>

The properties of a light-emitting device are described below. The properties of a light-emitting device include, for example, the initial properties of the light-emitting device, a result of a reliability test on the light-emitting device (sometimes referred to as the reliability of the light-emitting device), and the like.

Examples of the initial properties of a light-emitting device include a luminance—current density property, a current efficiency—luminance property, a luminance—voltage property, a current—voltage property, an external quantum efficiency—luminance property, a chromaticity—luminance property, an emission spectrum, and the like.

Examples of a reliability test on a light-emitting device include a test in which the initial luminance is set at a certain value, the driving of the light-emitting device is performed under a condition of a constant current density, and a change in luminance over the driving time is measured. At this time, the luminance may be a normalized luminance with the initial luminance of 100%. As a reduction in luminance over the deriving time is smaller, a light-emitting device has more favorable reliability.

Data on the properties of a light-emitting device, such as the initial properties of the light-emitting device and the reliability of the light-emitting device, are bivariate data, and it is quantified in many cases.

The above is the description of the properties of a light-emitting device.

<<Learning Data Set>>

Here, a learning data set used for supervised learning will be described.

FIG. 6A and FIG. 6B are diagrams illustrating structures of a learning data set 50. The learning data set 50 includes learning data 51_1 to learning data 51_m (m is an integer greater than or equal to 2). The learning data 51_1 to the learning data 51_m each include input data 52_1 to input data 52_m and teacher data 53_1 to teacher data 53_m. Note that the learning data 51_1 to the learning data 51_m respectively include information on a light-emitting device 10_1 to a light-emitting device 10_m and data on the properties of the light-emitting device 10_1 to the light-emitting device 10_m.

A target to be predicted in this embodiment is the properties of a light-emitting device. As described above, the properties of a light-emitting device are affected by the kind of an organic compound used for the intermediate layer 25, the kind of a conductive material used for the layer 20(1) and the layer 20(n) functioning as electrodes, the thicknesses of the layer 20(1) and the layer 20(n), the concentration ratio of a plurality of organic compounds in a layer including the plurality of organic compounds, and the like. Thus, these kinds of data are preferably included in the learning data set.

Figure 1B:
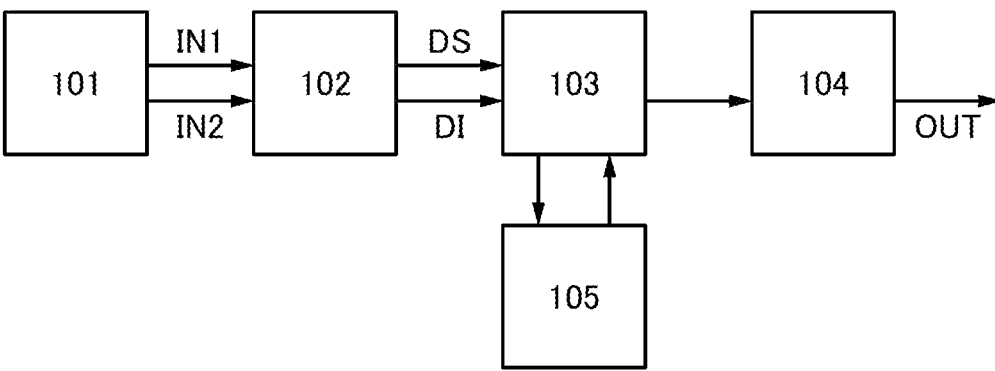

The learning set 50 is generated in the processing portion 102 illustrated in FIG. 1A and FIG. 1B. The data IN1 input to the processing portion 102 includes the information on the light-emitting devices, the data on the properties of the light-emitting devices, and the like. Thus, the learning data set is generated by performing extraction and processing or conversion on data included in the data IN1.

Note that data included in a learning data set used for supervised learning is preferably quantified. As compared with the case where the learning data set includes data other than a numerical value, in the case where the data included in the learning data set is quantified, a machine learning model can be prevented from being complicated.

In the learning data set 50 illustrated in FIG. 6A, the input data 52_1 to the input data 52_m include the information on the light-emitting device 10_1 to the light-emitting device 10_m, respectively. Furthermore, the teacher data 53_1 to the teacher data 53_m include the data on properties of the light-emitting device 10_1 to the light-emitting device 10_m.

As described above, the data on the properties of the light-emitting device 10_1 to the light-emitting device 10_m is quantified and thus can be respectively included in the teacher data 53_1 to the teacher data 53_m without particularly being converted. Note that characteristic points of the data on the properties of the light-emitting device 10_1 to the light-emitting device 10_m may be extracted and respectively included in the teacher data 53_1 to the teacher data 53_m. Furthermore, points may be extracted such that the values of control variables are at regular intervals and respectively included in the teacher data 53_1 to the teacher data 53_m.

Here, the information on the light-emitting device 10_1 to the light-emitting device 10_m will be described. First, the information on the light-emitting device 10_1 included in the input data 52_1 is described with reference to FIG. 6C.

The information on the light-emitting device includes the structure of the light-emitting device, the manufacturing conditions (process conditions) of the light-emitting device, and the like.

Examples of the information on the light-emitting device structure include the thickness of each layer, a material contained in each layer, the concentration ratio of the material contained in each layer, and the like. Examples of the information on the manufacturing conditions of the light-emitting device include the kind (e.g., shape) of an evaporation source, the evaporation rate, the deposition temperature, the state (e.g., the degree of vacuum) of an evaporation chamber, or an atmosphere to which the light-emitting device in the deposition process is exposed, the purity of an organic compound of an evaporation source (e.g., the kind of a contained impurity), the kind of a measuring apparatus, the kind of a deposition apparatus, a deposition method, and the like.

As illustrated in FIG. 6C, for example, the information on the structure of the light-emitting device 10_1 is included in the input data 52_1, as the information on the light-emitting device 10_1. Specifically, the information includes the thickness of each of the layer 20(1) to the layer 20(n) (thickness 22(1) to thickness 22(n)), one or more materials contained in each of the layer 20(1) to the layer 20(n) (a material 21(1) to a material 21(n)), the concentration ratio of one or more materials contained in each of the layer 20(1) to the layer 20(n) (concentration ratio 23(1) to concentration ratio 23(n)), or the like. Hereinafter, the thickness 22(1) to the thickness 22(n) are collectively referred to as thickness 22 in some cases. Furthermore, the material 21(1) to the material 21(n) are collectively referred to as a material 21 in some cases. In addition, the concentration ratio 23(1) to the concentration ratio 23(n) are collectively referred to as concentration ratio 23 in some cases.

The concentration ratio 23 included in the input data is preferably represented by the weight ratio in a layer. For example, in the case where one layer is formed by mixing a material A and a material B with a weight ratio of A:B=p:q (wt %) (p and q are each a real number greater than or equal to 0), the concentration ratio 23 included in the input data is preferably represented as p:q. In the case where one layer includes only the material A, the concentration ratio 23 included in the input data is preferably represented as 1:0 or 0:0. Furthermore, for example, in the case where three materials are mixed is assumed, the concentration ratio 23 included in the input data may be represented as p:q:r (r is a real number greater than or equal to 0).

Note that the concentration ratio 23 included in the input data is not limited to the case of being represented by weight ratio and may be represented by molar concentration ratio. Furthermore, the concentration ratio 23 included in the input data is not limited to the case of being represented by the concentration ratio in a layer and may be represented by the concentration ratio at the time of co-evaporation. In addition, the concentration ratio 23 included in the input data is not limited to the case of being represented by a ratio such as p:q and may be represented by a proportion of q/p.

The unit of thickness is preferably the same among the thickness 22(1) to the thickness 22(n). When the unit of thickness is the same, the volume of data included in the learning data set 50 can be reduced. Thus, the time spent for data transmission and reception, supervised learning, inference, or the like can be reduced.

As described above, the data included in a learning data set used for supervised learning is preferably quantified. The thickness 22 and the concentration ratio 23 are input as numerical values and thus can be included in the input data 52_1 without particularly being converted.

In contrast, as the data IN1, information on the organic compound contained in the light-emitting device is input as data other than a numerical value, such as a structural formula, a molecular structure noted by the SMILES (Simplified molecular input line entry specification syntax) notation (sometimes simply referred to as a molecular structure), a name determined by the IUPAC nomenclature of chemical compounds, or the like, in many cases. Thus, the information on the organic compound input as data other than a numerical value (e.g., a molecular structure) is preferably quantified.

An example of a method of quantifying a molecular structure is a method of replacing the molecular structure with the physical properties of an organic compound represented by the molecular structure. Examples of the physical properties of the organic compound include an emission spectrum, an absorption spectrum, a transmission spectrum, a reflectance spectrum, an S1 level, a T1 level, an oxidation potential, a reduction potential, a HOMO level, a LUMO level, a glass transition point, a melting point, a crystallization temperature, carrier mobility, and the like. These physical properties can be regarded as numerical values; however, much energy is needed to generate a learning data set because measurement and simulation need to be performed.

Thus, in one embodiment of the present invention, a molecular structure identifying the material 21 is converted by a certain method. The method is employed as long as molecular similarity can be expressed. As a method of expressing molecular similarity, quantitative structure-activity relationship (QSAR), Fingerprints, a graph structure, and the like are well known. For example, it is preferable that the molecular structure be quantified by a linear notation or a matrix notation. The quantified molecular structure identifying the material 21 can be used as learning data.

In the case where the structure of an inorganic compound is quantified, a descriptor such as a radial distribution function (RDF), Orbital Field Matrix (OFM), or the like is used.

[Example of Quantification of Molecular Structure of Organic Compound]

Here, an example of quantification (mathematization) of the molecular structure of an organic compound will be described.

In the case where the information on an organic compound is input as data other than a numerical value that is not in the SMILES notation, it is preferable that the information be converted into the SMILES notation first. Since an organic compound is noted as a consecutive character string in the SMILES notation, it is preferable as data for a computer. The SMILES notation and a fingerprinting method that is described later are classified into linear notation methods and preferable because mutual conversion is easily performed.

For the quantification of a molecular structure, RDKit, which is an open-source cheminformatics toolkit, can be used. In the RDKit, the SMILES notation of the input molecular structure can be converted into mathematical expression data (quantified) by a fingerprinting method.

Figure 7:
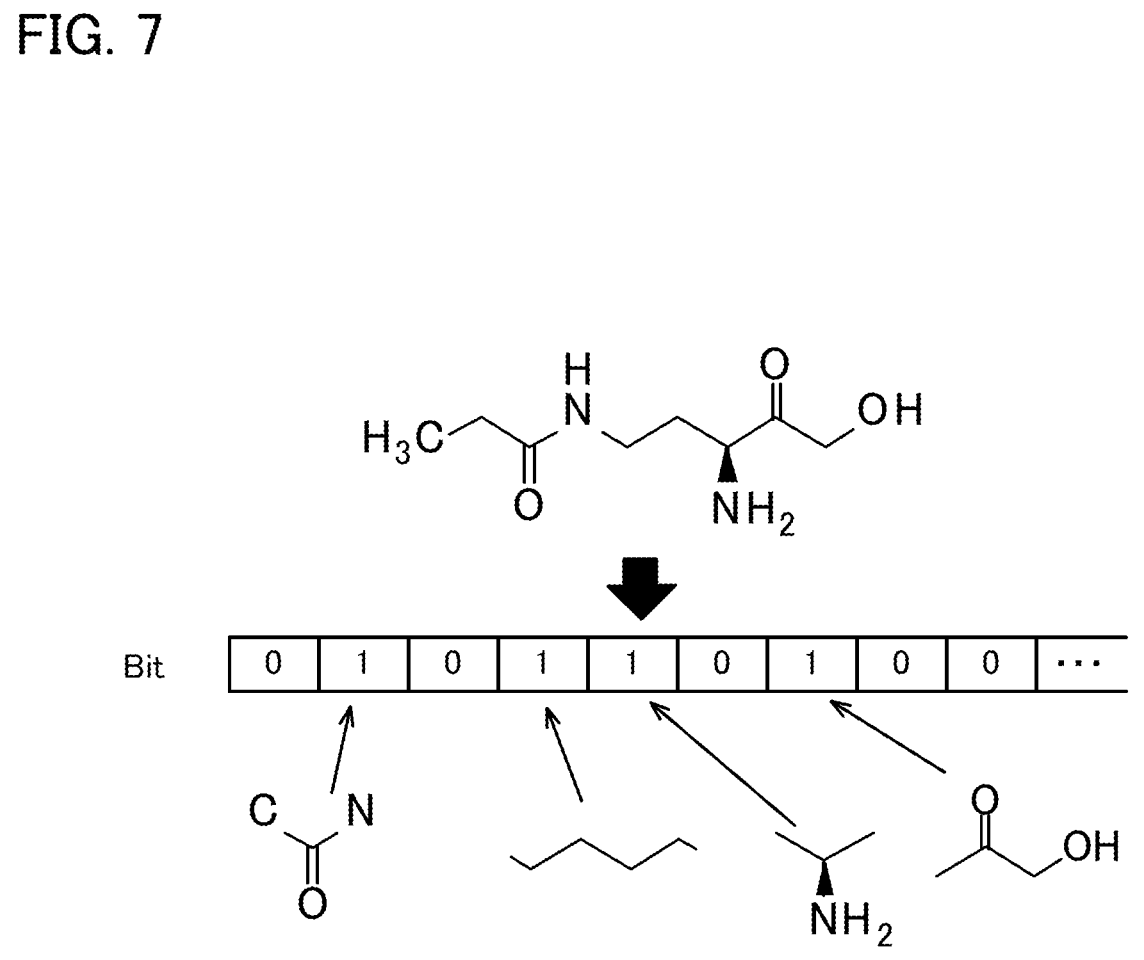

In a fingerprinting method, as illustrated in FIG. 7, for example, substructures (fragments) of a molecular structure are assigned to the respective bits to represent the molecular structure; "1" is set to the bit if the corresponding substructure is present in the molecule and "0" is set to the bit if the corresponding substructure is absent. That is, the fingerprinting method can provide a mathematical expression by extracting features of a molecular structure. In general, in an expression of a molecular structure expressed by a fingerprinting method, the bit length is several hundreds to several tens of thousands, which is a size easy to handle. Since a molecular structure is represented by a mathematical expression of 0 and 1, the use of a fingerprinting method enables significantly high-speed calculation processing.

There are many kinds of fingerprinting methods (methods considering the difference in bit generation algorithm, atom types or bond types, or conditions of aromaticity, methods dynamically generating a bit length using a hash function, or the like), which have different features.

FIG. 8A to FIG. 8D illustrate examples of kinds of a fingerprinting method. The following are typical kinds of fingerprinting methods: Circular type illustrated in FIG. 8A (neighboring atoms within a specified radius from the atom as a starting point are considered a substructure); Path-based type illustrated in FIG. 8B (atoms at a specified length of path (path length) from the atom as a starting point are considered a substructure); Substructure keys type illustrated in FIG. 8C (a substructure is defined for each bit); Atom pair type illustrated in FIG. 8D (atom pairs generated for all the atoms in a molecule are considered a substructure); and the like. The RDKit is equipped with these various types of fingerprints.

Figure 9:
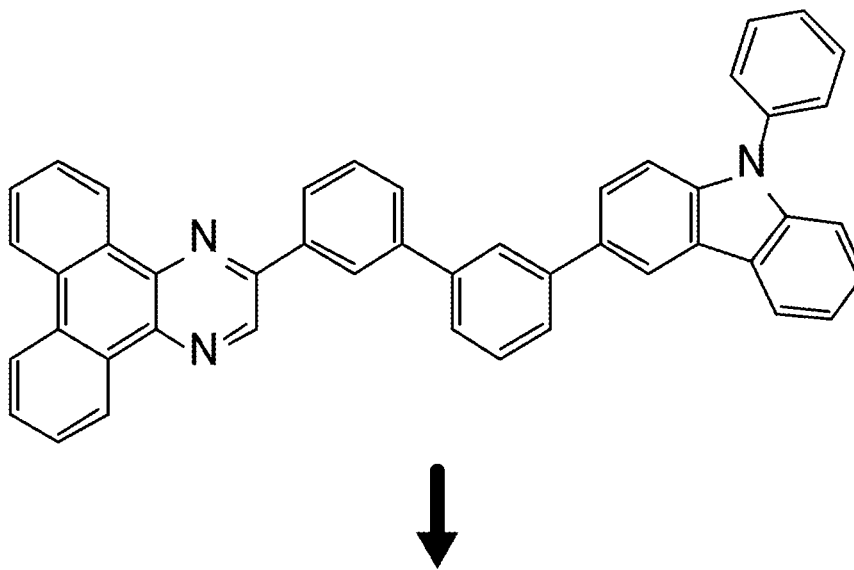
FIG. 9 is a diagram illustrating conversion from the SMILES notation to a notation by a fingerprinting method.
Figure 9:
Figure 9:

FIG. 9 is an example in which the molecular structure of a certain organic compound is actually represented as a mathematical expression by a fingerprinting method. In this manner, the molecular structure is once converted into the SMILES notation and then can be converted into a fingerprint.

When molecular structures of organic compounds are expressed by a fingerprinting method, different organic compounds having similar structures are represented by the same mathematical expression in some cases. As described above, there are some kinds of fingerprinting methods depending on notation methods; the tendencies for compounds to have the same mathematical expression are different among the notation methods as shown in the Circular type (Morgan Fingerprint), the Path-based type (RDK Fingerprint), the Substructure keys type (Avalon Fingerprint), and the Atom pair type (Hash atom pair) in FIG. 10. Molecules within the corresponding double-headed arrow show the same mathematical expression (notation) in FIG. 10. Thus, as a fingerprinting method used for learning, a fingerprinting method is preferably used with which the notations of organic compounds are all different when the molecular structures of the organic compounds to be learned are noted using at least one of the fingerprinting methods. FIG. 10 reveals that different compounds can be noted without duplicating notations by the Atom pair type. However, depending on the population of organic compounds to be learned, notation without duplicating notations can also be possible by another notation method in some cases.

Figure 11A:
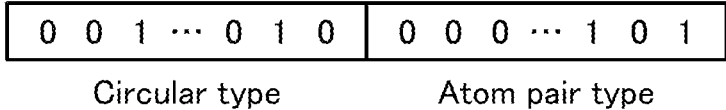
FIG. 11A and FIG. 11B are diagrams illustrating examples in which a molecular structure is noted by a plurality of fingerprinting methods.
Figure 11B:
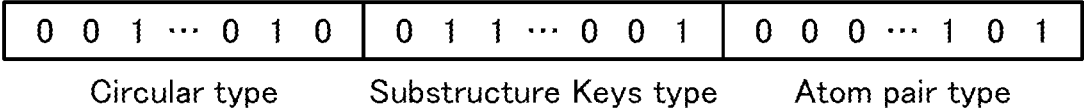

Then, when the molecular structure of an organic compound is represented by a fingerprinting method, it is preferable that a plurality of kinds of fingerprinting methods be used. Although any number of kinds may be used, two or three kinds or so are manageable in terms of the volume of data and preferred. When a plurality of kinds of fingerprinting methods are used, the molecular structure of an organic compound may be described in such a manner that a mathematical expression noted by one kind of fingerprinting method is followed by a mathematical expression noted by another kind of fingerprinting method, or the molecular structure of an organic compound may be described with the assumption of the presence of a plurality of kinds of different mathematical expressions for one organic compound. FIG. 11A and FIG. 11B show examples of methods in which a plurality of fingerprints of different types are used to describe the molecular structure of an organic compound.

A fingerprinting method is a method of describing the presence or absence of a substructure, in which information on the whole molecular structure is lost. However, when a molecular structure is mathematized using a plurality of fingerprints of different types, different substructures are generated by the respective types of fingerprints, so that information about the presence or absence of these substructures can complement information on the whole molecular structure. In the case where a feature that cannot be sufficiently expressed by a certain fingerprint affects the properties of a light-emitting device significantly, the method of describing a molecular structure using a plurality of fingerprints of different types is effective because the feature is complemented by another fingerprint.

As shown in FIG. 11A, the Atom pair type and the Circular type are preferably used for notation by two kinds of fingerprinting methods because physical property prediction can be accurately performed in this structure.

As shown in FIG. 11B, the Atom pair type, the Circular type, and the Substructure keys type are preferably used for notation by three kinds of fingerprinting methods, because physical property prediction can be accurately performed in this structure.

In the case where the Circular-type fingerprinting method is used, a radius r is preferably greater than or equal to 3, further preferably greater than or equal to 5. The term radius r is the number of bonded atoms counted starting from a certain atom as 0.

In the case where a fingerprinting method to be used is selected, at least one with which the notations of organic compounds are all different when the molecular structures of the organic compounds are noted is preferably selected as described above.

Although an increase in bit length (the number of bits) to be expressed can reduce the possibility of generating the notations of organic compounds which agree exactly with each other, a fingerprint has a trade-off problem that an excessive increase in bit length increases the calculation cost or the database management cost. When a plurality of fingerprints are used at the same time for expression, the different fingerprint types in combination might avoid an exact agreement between notations of a plurality of molecular structures as a whole even if the notations agree exactly with each other according to one fingerprint type. This can allow the shortest possible bit length to create a state where no organic compounds have exactly the same notations by fingerprints. There is no particular limitation on the bit lengths of fingerprints to be generated. However, in consideration of the calculation cost or the database management cost, when molecules each have a molecular weight up to approximately 2000 and the bit length for each fingerprint type is 4096 or less, preferably 2048 or less, or even 1024 or less depending on cases, a fingerprint in which organic compounds do not have exactly the same notation can be generated.

The bit lengths of fingerprints generated by the respective fingerprint types are adjusted as appropriate in consideration of features of the types or the whole molecular structure, and not necessarily the same. For example, the bit lengths may be represented as 1024 bits in the Atom pair type and 2048 bits in the Circular type, and they may be connected to each other.

The above is the description of the quantification of the molecular structure of an organic compound.

According to the above, the learning data 51_1 including quantified data can be generated. The learning data 51_2 to the learning data 51_m including the quantified data have a structure similar to that of the learning data 51_1.

In the case where information on a light-emitting device including k (k is an integer greater than or equal to 3 and less than or equal to (n–1)) layers is made to be included in learning data, zero is preferably input (zero padding is preferably performed) with respect to the material 21($k$+1) to the material 21($n$), the thickness 22($k$+1) to the thickness 22($n$), and the concentration ratio 23($k$+1) to the concentration ratio 23($n$) in the learning data.

The value of n is preferably specified in a learning data set. When the value of n is fixed, the number of neurons (units) included in the input layer IL can be determined.

It is preferable that n be greater than or equal to 5, further preferably greater than or equal to 7. Although there is no particular limitation on the upper limit of n, when the value of n is too large, the number of neurons included in the input layer IL is increased, which might increase the time spent for supervised learning and inference. Therefore, n is preferably less than or equal to 30, for example.

In some cases, each of the input data 52_1 to the input data 52_m does not necessarily include the information on the layer 20(1) and the layer 20($n$) that are the anode or the cathode of the light-emitting device 10. In this case, the volume of data included in the learning data set 50 is reduced. Thus, the time spent for data transmission and reception, supervised learning, or inference can be reduced.

FIG. 6A illustrates the case where the input data 52_1 to the input data 52_m respectively include the information on the light-emitting device 10_1 to the light-emitting device 10_m, but the present invention is not limited thereto. For example, as illustrated in FIG. 6B, the input data 52_1 to the input data 52_m may respectively include the information on the light-emitting device 10_1 to the light-emitting device 10_m and data on first properties of the light-emitting device 10_1 to the light-emitting device 10_m, and the teacher data 53_1 to the teacher data 53_m may respectively include data on second properties of the light-emitting device 10_1 to the light-emitting device 10_m.

In the above case, the first properties of the light-emitting device 10_1 to the light-emitting device 10_m and the second properties of the light-emitting device 10_1 to the light-emitting device 10_m are made to be different form each other. For example, it is preferable that the initial properties of the light-emitting device 10 be used as the first property of the light-emitting device 10, and the reliability of the light-emitting device 10 be used as the second property of the light-emitting device 10. The reliability of the light-emitting device is affected by a lot of factors, and the factors influence each other complicatedly; thus, the reliability is difficult to predict with experiences and a preferable target to be estimated. The initial properties of the light-emitting device 10 indirectly include information such as the manufacturing conditions and the measurement conditions of the light-emitting device. Thus, when the first property of the light-emitting device 10 is added to the input data, the information is provided to supervised learning, and thus the accuracy of the reliability prediction of the light-emitting device can be improved.

FIG. 6C illustrates the case where the input data 52_1 to the input data 52_m respectively include the information on the structures of the light-emitting device 10_1 to the light-emitting device 10_m, but the input data 52_1 to the input data 52_m are not limited thereto. For example, as illustrated in FIG. 6D, the input data 52_1 to the input data 52_m may respectively include the information on the structures of the light-emitting device 10_1 to the light-emitting device 10_m and the information on the manufacturing conditions of the light-emitting devices. For example, it is preferable that the input data 52_1 include the material 21(1), the thickness 22(1), the concentration ratio 23(1), evaporation rate 31(1) of the material 21(1), a deposition temperature 32(1) of the material 21(1), and the like.

Note that the learning data set 50 may be composed of only data on light-emitting devices having the same color or similar emission colors. In other words, the learning data set 50 may be formed for each emission color. This leads to an increase in the accuracy of the property prediction of a light-emitting device. The learning data set 50 may be composed of data on light-emitting devices regardless of an emission color. This enables versatile property prediction of a light-emitting device.

The above is the description of the learning data set. The use of the input data and the teacher data for the training of a machine learning model enables the property prediction of a light-emitting device. Note that in the case where the initial properties of a light-emitting device are predicted, it is preferable that the information on the light-emitting device structure be included in the input data and the initial properties of the light-emitting device be provided as the teacher data.

<<Data Used for Property Prediction>>

Here, data used for property prediction will be described.

The data used for the property prediction is generated in the processing portion 102 illustrated in FIG. 1A and FIG. 1B. The data IN2 input to the processing portion 102 includes at least the information on the light-emitting device structure. Furthermore, the data IN2 includes the data such as the properties of the light-emitting device in some cases.

Note that data used for property prediction preferably has a structure similar to that of the input data of the learning data. For example, in the case where the information on the light-emitting device structure is included in the input data of the learning data, the information on the light-emitting device structure is preferably included in the data used for property prediction. For example, in the case where the information on the light-emitting device structure and the data on the properties of the light-emitting device are included in the input data of the learning data, the information on the light-emitting device structure and the data on the properties of the light-emitting device are preferably included in the data used for property prediction.

Specifically, the data used for property prediction includes the thickness 22(1) to the thickness 22($n$), the material 21(1) to the material 21($n$), the concentration ratio 23(1) to the concentration ratio 23($n$), and the like.

The above is the description of the data used for property prediction.

Accordingly, one embodiment of the present invention can provide a method of predicting the properties of a light-emitting device. Another embodiment of the present invention can provide a property prediction system predicting the properties of a light-emitting device.

According to one embodiment of the present invention, the properties of a light-emitting device can be predicted without the use of the physical properties of an organic compound contained in a light-emitting device, or the like. Furthermore, the use of the previous experiment data enables the light-emitting device structure to be optimized at high speed by virtual screening. Even if interpolation is not performed when people see data, interpolation is sometimes performed with a nonlinear or high-order expression of a machine learning model. Furthermore, when the expression obtained by the machine learning model is cut out fragmentarily and studied, the regularity that has not been found can be seen.

Parts of this embodiment can be combined as appropriate for implementation.

REFERENCE NUMERALS

DI: data, DS: learning data set, HL: hidden layer, IL: input layer, IN1: data, IN2: data, OL: output layer, OUT: data, 10: light-emitting device, 10_1: light-emitting device, 10_m: light-emitting device, 20: layer, 21: material, 22: thickness, 23: concentration ratio, 25: intermediate layer, 31: evaporation rate, 32: deposition temperature, 50, learning data set, 51_1: learning data, 51_2: learning data, 51_m: learning data, 52_1: input data, 52_m: input data, 53_1, teacher data, 53_m: teacher data, 100: property prediction system, 101: input portion, 102: processing portion, 103: arithmetic portion, 104: output portion, 105: memory portion This application is based on Japanese Patent Application Serial No. 2019-156559 filed on Aug. 29, 2019, the entire contents of which are hereby incorporated herein by reference.

The invention claimed is:

1. A method for predicting a property of a light-emitting device, the method comprising:

inputting first data and second data, generating a learning data set comprising first learning data and second learning data, the first learning data generated from the first data and the second learning data generated from the second data, performing supervised learning on the basis of the learning data set, inputting third data, generating data used for predicting the property of the light-emitting device from the third data, making an inference of at least one of initial properties and reliability of the light-emitting device from the data used for predicting the property of the light-emitting device on the basis of the learning result of the supervised learning, and outputting fourth data including at least one of the initial properties and the reliability of the light-emitting device, wherein the first learning data includes information of a structure of a first light-emitting device, information of a first organic compound included in the first light-emitting device, information of initial properties of the first light-emitting device, and information of reliability of the first light-emitting device, wherein the second learning data includes information of a structure of a second light-emitting device, information of a second organic compound included in the second light-emitting device, information of initial properties of the second light-emitting device, and information of reliability of the second light-emitting device, and wherein the data used for predicting the property of the light-emitting device includes information of a structure of the light-emitting device and information of an organic compound included in the light-emitting device.

2. The method according to claim 1, wherein the information of the first organic compound included in the first light-emitting device comprise molecular structure of the first organic compound, wherein the information of the second organic compound included in the second light-emitting device comprise molecular structure of the second organic compound, wherein the information of the organic compound included in the light-emitting device comprises molecular structure of the organic compound, wherein the first learning data comprises a quantified molecular structure of the first organic compound included in the first light-emitting device, wherein the second learning data comprises a quantified molecular structure of the second organic compound included in the second light-emitting device, and wherein the data used for predicting the property of the light-emitting device comprises a quantified molecular structure of the organic compound included in the light-emitting device.

3. The method according to claim 1, wherein the initial properties of the first light-emitting device comprise any one of a luminance-current density property, a current efficiency-luminance property, a luminance-voltage property, a current-voltage property, an external quantum efficiency-luminance property, a chromaticity-luminance property, and an emission spectrum, and wherein the initial properties of the second light-emitting device comprise any one of a luminance-current density property, a current efficiency-luminance property, a luminance-voltage property, a current-voltage property, an external quantum efficiency-luminance property, a chromaticity-luminance property, and an emission spectrum.

4. The method according to claim 2, wherein the quantified molecular structure of the first organic compound, the quantified molecular structure of the second organic compound, and the quantified molecular structure of the organic compound are obtained by quantitative structure-activity relationship or a fingerprinting method.

5. The method according to claim 1, wherein a neural network is used for the supervised learning, and wherein the neural network comprises two or more hidden layers between an input layer and an output layer.

6. The method according to claim 1, wherein a learned model generated by the supervised learning is stored in a memory portion.

7. A method for predicting a property of a light-emitting device, the method comprising:

inputting first data, generating data used for predicting the property of the light-emitting device from the first data, and making an inference of at least one of initial properties and reliability of the light-emitting device from the data used for predicting the property of the light-emitting device by using a neural network, wherein the data used for predicting the property of the light-emitting device includes information of a structure of the light-emitting device and a quantified molecular structure of the organic compound included in the light-emitting device.

8. The method according to claim 7, wherein the initial properties of the light-emitting device comprise any one of a luminance-current density property, a current efficiency-luminance property, a luminance-voltage property, a current-voltage property, an external quantum efficiency-luminance property, a chromaticity-luminance property, and an emission spectrum.

9. The method according to claim 7, wherein the quantified molecular structure of the organic compound is obtained by quantitative structure-activity relationship or a fingerprinting method.

\* \* \* \* \*